(12) United States Patent
Abraham

(10) Patent No.: US 6,798,513 B2
(45) Date of Patent: Sep. 28, 2004

(54) MEASURING MODULE

(75) Inventor: Michael Abraham, Mainz (DE)

(73) Assignee: NanoPhotonics AB (DE)

( * ) Notice: Subject to any disclaimer, the term of this patent is extended or adjusted under 35 U.S.C. 154(b) by 73 days.

(21) Appl. No.: 10/120,641

(22) Filed: Apr. 11, 2002

(65) Prior Publication Data

US 2003/0193660 A1 Oct. 16, 2003

(51) Int. Cl.⁷ .................................................. G01J 4/00
(52) U.S. Cl. ..................................................... 356/369
(58) Field of Search ................................. 356/326, 369, 356/630, 237.4, 237.5

(56) References Cited

U.S. PATENT DOCUMENTS

| | | | | |
|---|---|---|---|---|
| 5,179,863 A | * | 1/1993 | Uchida et al. ............... 356/505 |
| 5,194,743 A | * | 3/1993 | Aoyama et al. ............. 356/400 |
| 5,502,567 A | | 3/1996 | Pokrowsky et al. |
| 5,546,179 A | * | 8/1996 | Cheng .......................... 356/73 |
| 5,694,214 A | * | 12/1997 | Watanabe et al. ......... 356/237.2 |
| 5,790,252 A | * | 8/1998 | Masumura et al. .......... 356/450 |
| 5,959,732 A | * | 9/1999 | Hara et al. ................... 356/500 |
| 6,091,499 A | | 7/2000 | Abraham et al. |
| 6,181,427 B1 | | 1/2001 | Yarussi et al. |
| 6,342,942 B1 | * | 1/2002 | Uzawa ........................ 356/399 |
| 6,368,182 B2 | * | 4/2002 | Dvir et al. ................... 356/503 |
| 6,421,112 B1 | * | 7/2002 | Bisschops et al. ............ 355/53 |
| 6,473,186 B2 | * | 10/2002 | Kawasaki et al. ........... 356/512 |
| 2002/0096640 A1 | * | 7/2002 | Tanaka ........................ 250/397 |

* cited by examiner

*Primary Examiner*—Michael P. Stafira
*Assistant Examiner*—Juan D Valentin, II
(74) *Attorney, Agent, or Firm*—Hudak, Shunk & Farine Co. LPA

(57) ABSTRACT

The present invention relates to a measuring module, whose measuring device comprises a measuring head equipped with a miniaturized measuring unit, and a spatially separately arranged control and evaluation unit, and wherein the measuring head is arranged so as to be able to slide linearly by means of a sliding drive.

2 Claims, 2 Drawing Sheets

MEASURING MODULE

FIELD OF THE INVENTION

The invention concerns a measuring module for measuring the surface of wafers with a measuring head and a measuring table, which is equipped with a wafer accommodation.

BACKGROUND OF THE INVENTION

For quality control purposes, so-called "integrated measuring technology" is increasingly used in the manufacture of semi-conductor chips, in particular for the manufacture of wafers with a diameter of 300 mm. With integrated measuring technology the measuring device, in contrast to conventional "stand-alone" measuring technology, is directly linked to and integrated into the manufacturing equipment, so as to allow quality monitoring to be performed as close to the process as possible.

The integration of measuring technology into process equipment is often associated with very high expense, since changes to both systems, or rather to the process equipment and the measuring systems, are often necessary, which, in turn, entails additional costs.

However, in 300 mm wafer technology there is a high level of standardization. The process devices are equipped with so-called "Equipment Front End Modules" (EFEM). The EFEM's represent the interface between the chip factory and the process device and provide logistics, or rather the automatic loading of the equipment with wafers. The EFEM's generally have at least two load ports, whose dimensions are standardized. The containers (Front Opening Unified Pod, FOUP) containing the wafers are stopped on the load ports. The EFEM also has a robot and is connected to the current process device on the back. The EFEM contains a wafer container (FOUP), supplies the wafers to the process device by means of a port, with the aid of another robot, and again feeds the wafers to an FOUP after the process.

In principle, an EFEM can also have several load ports. The load ports can easily be changed out. The EFEM is thus an ideally suited place for connecting a measuring device to process equipment, because in doing so the available logistics of the EFEM can be used with robots anyway to integrate the measuring procedure into the manufacturing process in a flexible way.

With the aid of integrated measuring technology it is possible to feed the wafers for measurement upon entry, prior to the process, and for final control after the process. This makes it possible to avoid any further processing of defective wafers and resupply the equipment through the process window provided if deviations in parameters are determined.

A prerequisite for attaching the measuring module to the EFEM, instead of a load port, is however that the measuring devices not be any wider or deeper than a load port, and must therefore keep to standardized dimensions.

Since, however, with most measuring procedures, the entire wafer must be examined, with its diameter of 300 mm, considerable problems arise in observing these standardized measurements.

Devices and procedures are known that do not adhere to these standardized dimensions. It is known from current technology that measuring device 1 must be installed in a stationary position and the wafer 3 in a moveable position, as shown in FIG. 1a. The measuring point is indicated as 4. This variant is quite widespread, because the measuring devices 1 are often very large and are too sensitive to be able to be moved. If an XY pathway is used, then the required surface, indicated by the frame 2, must amount to at least 600×600 mm (see FIG. 1a), so that the width of the load port is significantly exceeded.

From U.S. Pat. No. 6,181,427 the so-called "R Theta Procedure" is known, with which a translatory movement is replaced by the rotation of the wafer 3. The measuring device 1', which is smaller than measuring device 1, is translatorily moved by half of the diameter of the wafer. This does achieve a reduction in the footprint, although the minimum required surface (frame 2') still amounts to 300× 450 mm, as shown in FIG. 1b. Through the combination of a complete revolution and a translation around half of the diameter of the wafer, any point can be reached. This method allows for a significantly more compact construction, whereby the critical width of the load ports is however not exceeded, although a dimension of at least 450 mm is achieved in the depth. In practice, however, this value is higher, since there is also a footprint for the measuring device 1'.

The problem of the invention consists of finding a measuring module with a compact construction, so that a surface area of 450×450 mm is not exceeded.

SUMMARY OF THE INVENTION

This problem is solved with a measuring module, whose measuring device comprises a measuring head equipped with a miniaturized measuring unit, and a spatially separately arranged control and evaluation unit, and that the measuring head is arranged so as to be able to slide linearly by means of a sliding drive.

By "Miniaturized Measuring Device" a device is understood, whose footprint covers <150×300 mm. Such measuring units, for example, are known from U.S. Pat. No. 5,502,567 or U.S. Pat. No. 6,091,499.

Since the control and evaluation unit is spatially arranged separately, such as under the measuring table or even outside the available surface, these components of the measuring device do not need to be moved. The measuring head can therefore be designed in a compact way and the sliding drive can accordingly be designed in a lower-performance and thus also more compact way.

The control and evaluation unit, as an example, is connected to the measuring head by means of a cable or infrared path.

Such a miniaturized measuring head offers the advantage that it not only has a small footprint, but it can also be designed to be robust through its reduction to the most necessary components. Thus a compact and reasonably priced measuring module is created, which remains within the standardized dimensions of a load port and can thus be integrated into the wafer process equipment without a problem, without any changes having to be made to the process equipment itself.

By preference, The rotation drive is a rotation motor arranged under the wafer accommodation. The immediate arrangement of the rotation motor under the accommodation saves space, since no additional footprint is therefore required.

The sliding drive by preference comprises two linear motors arranged on two opposing sides of the wafer accommodation.

By preference, both linear motors are connected to each other by a support extending over the wafer accommodation, on which the measuring head is arranged.

The measuring unit integrated into the measuring head may, for example, be a spectrometer for measuring layer thickness and composition, an FTIR spectrometer for measuring impurities, an Ellipsometer for measuring layer thickness, a microscope for measuring lateral structures, as well as defects, a scattered light measuring device for measuring particles and other defects, or an atomic force microscope.

BRIEF DESCRIPTION OF THE DRAWINGS

Exemplary embodiments of the invention are explained in further detail below with the use of the following drawings FIGS. 1a+1b schematic arrangements for illustrating the footprint of measuring devices according to current technology, FIG. 2 schematic representation to illustrate the footprint with the use of an invention-related measuring module, FIG. 3a view from above of a measuring module, and FIG. 3b side view of the measuring module shown in FIG. 3a.

DETAILED DESCRIPTION OF THE INVENTION

Figure 1A:
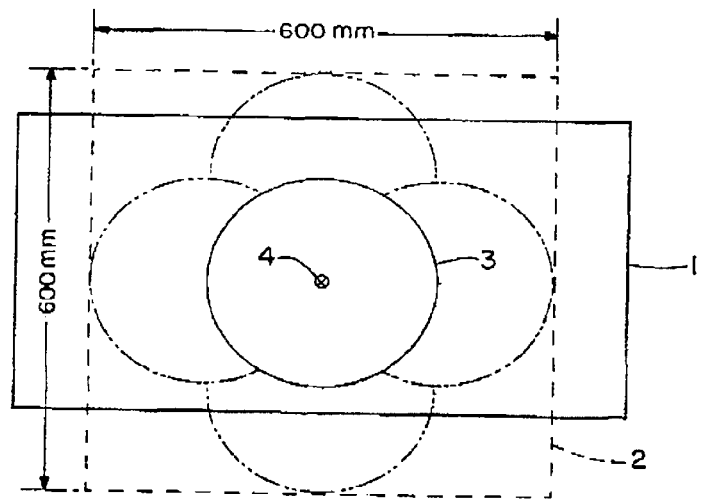
Figure 1B:
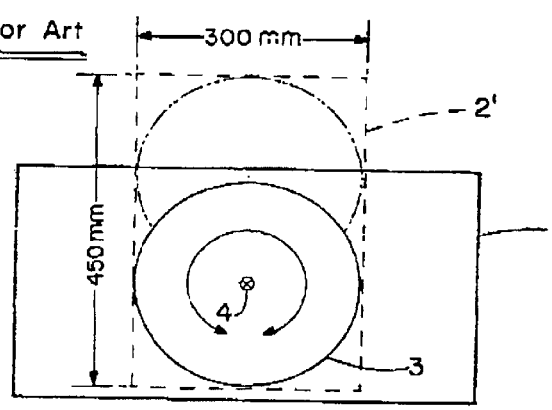
Figure 2:
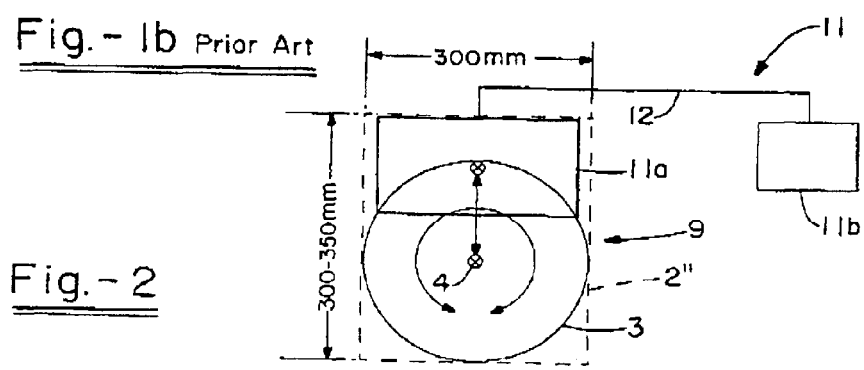

In FIG. 2 a measuring module 9 with a measuring device 11 is schematically represented, which comprises a measuring head 11a and a control and evaluation unit 11b, which, for example, are connected to each other by a cable 12. The dimensions of the measuring head 11a are under 150×300 mm. The measuring head 11a is shifted by means of a translatory movement, so that the measuring point 4 moves over the wafer 5, whereby a path is covered, which corresponds to half of the diameter of the wafer 3. The wafer 3 is rotated, so that no additional footprint is required for this. The total footprint required is indicated by the frame 2", drawn in a dashed line, which comprises the maximum dimensions of 300×350 mm.

The footprint of the measuring module 9 is thus clearly less than the dimensions of 350 mm (width) and 400 mm (depth).

Figure 3A:
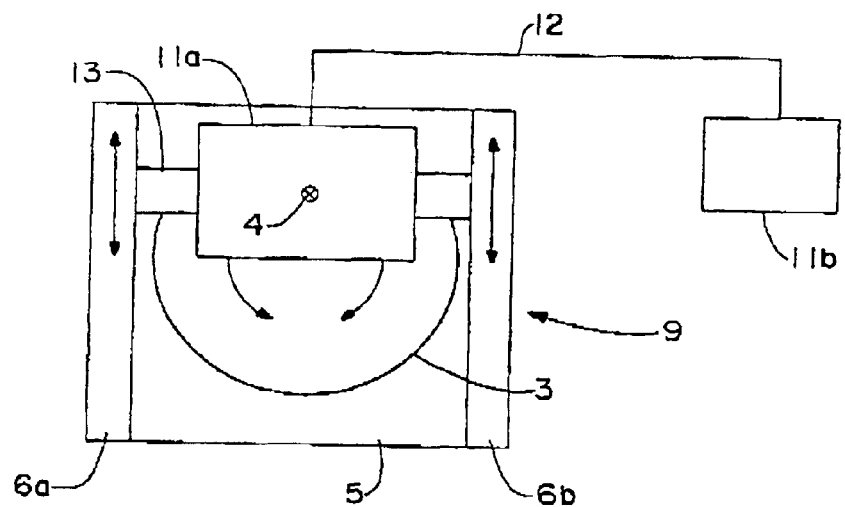
Figure 3B:
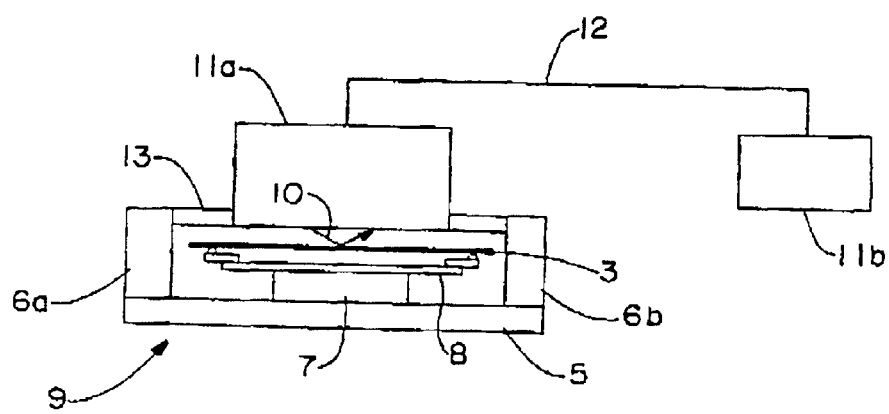

FIG. 3a shows the view from above of measuring module 9. The wafer 3 lies on a wafer accommodation 8 (see FIG. 3b), which forms a turntable in the depiction shown here, which is driven by a rotation motor 7, which in turn, is attached to a base plate 5. On the base plate 5, two linear motors 6a and 6b are arranged, laterally to the wafer accommodation 8, which are connected to each other by a support 13, on which the measuring head 11a is arranged. The beam 10 is directed toward the wafer 3 and the reflected light from the measuring head 11a is recorded and measured. The measuring head 11a is connected to a control and evaluation unit 11b.

REFERENCE NUMBERS

1 Measuring device
1' Measuring device
2 Footprint
2' Footprint
2" Footprint
3 Wafer
4 Measuring point
5 Base plate
6a, b Linear motor
7 Rotation motor
8 Wafer accommodation
9 Measuring module
10 Measuring ray
11 Measuring device
11a Measuring head
11b Control and evaluation unit
12 Cable
13 Support

What is claimed is:

1. A measuring module for measuring the surface of wafers not exceeding a surface area of 450×450 mm comprising: a measuring device and a measuring table, which comprises a wafer accommodation equipped with a rotation drive, wherein the measuring device comprises a measuring head fitted with a miniaturized measuring unit which is a spectrometer for measuring layer thickness and composition, an FTIR spectrometer for measuring impurities, an Ellipsometer for measuring layer thickness, a microscope for measuring lateral structures, as well as defects, a scattered light measuring device for measuring particles and other defects, or an atomic force microscope, and a spatially separate control and evaluation unit and that the measuring head is arranged to be linearly movable by means of a sliding drive, wherein the sliding drive comprises two linear motors arranged on two opposing sides of the wafer accommodation, and wherein both linear motors are connected to each other via a support extending over the wafer accommodation, on which the measuring head is arranged.

2. A measuring module according to claim 1, wherein the rotation drive is a rotation motor arranged under the wafer accommodation.

* * * * *

UNITED STATES PATENT AND TRADEMARK OFFICE
CERTIFICATE OF CORRECTION

PATENT NO. : 6,798,513 B2
DATED : September 28, 2004
INVENTOR(S) : Michael Abraham It is certified that error appears in the above-identified patent and that said Letters Patent is hereby corrected as shown below:

Title page,
Item [73], Assignee, please replace "NanoPhotonics AB" with -- NanoPhotonics AG --.

Signed and Sealed this

Nineteenth Day of April, 2005

JON W. DUDAS
*Director of the United States Patent and Trademark Office*